US007862548B2

(12) United States Patent
Javer et al.

(10) Patent No.: US 7,862,548 B2
(45) Date of Patent: Jan. 4, 2011

(54) NASAL IRRIGATION DEVICE

(75) Inventors: Amin R. Javer, Vancouver (CA); Ezra Kwok, Vancouver (CA); Brenda Lauk, Vancouver (CA); Kevin Wong, Vancouver (CA); Nael Shoman, Vancouver (CA); Bradford Mechor, Calgary (CA)

(73) Assignee: Bekan Rhinologics Inc., Vancouver, B.C. (CA)

( * ) Notice: Subject to any disclaimer, the term of this patent is extended or adjusted under 35 U.S.C. 154(b) by 188 days.

(21) Appl. No.: 12/030,737

(22) Filed: Feb. 13, 2008

(65) Prior Publication Data
US 2009/0202665 A1 Aug. 13, 2009

(51) Int. Cl.
 *A61M 3/00* (2006.01)
 *A61M 1/00* (2006.01)
(52) U.S. Cl. .................. 604/310; 604/94.01; 604/212; 604/540
(58) Field of Classification Search .................. 604/257, 604/275, 93.01, 94.01, 212, 258, 294, 310, 604/316, 540; 424/744
See application file for complete search history.

(56) References Cited

U.S. PATENT DOCUMENTS

| 690,527 | A | * | 1/1902 | Moores | 604/94.01 |
| 758,673 | A | * | 5/1904 | Meinecke | 604/191 |
| 858,996 | A | * | 7/1907 | Lamport | 604/94.01 |
| 1,481,008 | A | * | 1/1924 | Hodlick | 604/212 |
| 1,599,787 | A | * | 9/1926 | Meyer | 604/217 |
| 1,603,758 | A | * | 10/1926 | Fisher | 604/36 |
| 1,703,238 | A | * | 2/1929 | Hovis | 604/77 |
| 1,734,426 | A | * | 11/1929 | Graham | 604/212 |
| 1,755,754 | A | * | 4/1930 | Wappler et al. | 604/37 |
| 2,052,321 | A | * | 8/1936 | Smart | 604/94.01 |
| 2,135,052 | A | * | 11/1938 | Rose | 604/24 |
| 2,445,653 | A | * | 7/1948 | White | 128/200.14 |
| 2,612,894 | A | * | 10/1952 | Akins | 604/212 |
| 2,635,603 | A | * | 4/1953 | Smith | 604/217 |
| 2,945,495 | A | * | 7/1960 | Griffin | 604/257 |
| 3,066,669 | A | * | 12/1962 | De Melfy | 128/200.22 |
| 3,144,021 | A | * | 8/1964 | Diaz | 604/257 |
| 3,400,714 | A | * | 9/1968 | Sheridan | 128/207.18 |
| 3,625,213 | A | * | 12/1971 | Brown | 604/200 |
| 3,635,218 | A | * | 1/1972 | Ericson | 604/37 |
| 4,405,321 | A | * | 9/1983 | Budoff | 604/212 |
| 5,053,022 | A | * | 10/1991 | Bryant et al. | 604/278 |
| 5,477,852 | A | * | 12/1995 | Landis et al. | 128/207.18 |
| 5,787,799 | A | * | 8/1998 | Mohrhauser et al. | 99/345 |
| 5,817,066 | A | * | 10/1998 | Goforth | 604/212 |
| 5,899,878 | A | * | 5/1999 | Glassman | 604/48 |
| 6,228,070 | B1 | * | 5/2001 | Mezzoli | 604/257 |
| 6,238,377 | B1 | * | 5/2001 | Liu | 604/289 |
| 6,241,705 | B1 | | 6/2001 | Ko-Wen | |
| 6,361,521 | B1 | | 3/2002 | Erickson | |

(Continued)

*Primary Examiner*—Tatyana Zalukaeva
*Assistant Examiner*—Paula L Craig
(74) *Attorney, Agent, or Firm*—DLA Piper LLP (US)

(57) ABSTRACT

A nasal irrigation device includes a container for storing nasal cleansing fluid, a spout having a connecting end, a nose engaging end and a spout passage, the connecting end of the spout being removably coupled to the container to allow the spout passage to receive nasal cleansing fluid from an opening of the container, the spout having a curved portion for directing nasal cleansing fluid toward a nasal passageway of a user when the container is clear of a nasal discharge path, the spout passage being continually open and unobstructed. The container is partially collapsible to force nasal cleansing fluid through the spout passage and into the nasal passageway.

3 Claims, 8 Drawing Sheets

U.S. PATENT DOCUMENTS

| | | | |
|---|---|---|---|
| 6,383,173 B1 * | 5/2002 | Hunt | 604/533 |
| 6,485,451 B1 * | 11/2002 | Roberts et al. | 604/35 |
| 6,520,384 B2 | 2/2003 | Mehta | |
| 6,540,718 B1 | 4/2003 | Wennek | |
| 2002/0099331 A1 * | 7/2002 | Burchfield | 604/94.01 |
| 2002/0169422 A1 | 11/2002 | Ahnblad et al. | |
| 2003/0229306 A1 * | 12/2003 | Sherman | 604/93.01 |
| 2006/0253087 A1 * | 11/2006 | Vlodaver et al. | 604/275 |
| 2007/0142792 A1 * | 6/2007 | Terrill | 604/275 |
| 2007/0249896 A1 * | 10/2007 | Goldfarb et al. | 600/101 |
| 2008/0294124 A1 * | 11/2008 | Mehta | 604/260 |
| 2009/0200336 A1 * | 8/2009 | Koh | 222/173 |

* cited by examiner

NASAL IRRIGATION DEVICE

TECHNICAL FIELD

The present invention relates to a nasal irrigation device, in particular, a nasal irrigation device for rinsing a user's nasal passages using a saline solution delivered under pressure.

BACKGROUND

Rinsing of the nasal passages with a saline solution is a well tried method for alleviating allergies and infections and has been recommended by doctors for many years.

In the past, the nasal passages were either rinsed by sniffing the saline solution into the nose or inverting the nose and pouring the saline solution into the nose from a receptacle. These methods were both inefficient and uncomfortable for the user.

In order to improve upon the previous methods, a bottle having a nozzle for delivering saline solution under pressure was developed. By delivering the saline solution under pressure, the rinsing process is more effective and can be performed in a shorter period of time.

Although an improvement over the previous methods, the bottle has several disadvantages. Because the bottle is held under the nose and saline solution is sprayed upward into the nasal passages, used saline solution drips onto the user's hands, which is messy and unhygienic. In addition, the narrow passages provided in the bottle and/or nozzle are difficult to clean and even more difficult to dry. As a result, bacteria collect in the narrow passages and infect or re-infect the user each time the bottle is used. This can be very dangerous particularly if the bottle is used for long periods of time without sterilization. Despite significant efforts to clean the tubing and narrow passages in the currently available bottles, cultures taken from the tubing of used bottles have grown bacteria (*Staphyloccocus aureus*) in the laboratory.

It is therefore desirable to provide a nasal irrigation device that obviates or mitigates at least one of the disadvantages of the prior art.

SUMMARY

A nasal irrigation device comprising:

a container having an opening, the container for storing nasal cleansing fluid;

a spout having a connecting end, a nose engaging end and a spout passage, the connecting end of the spout being removably coupled to the container to allow the spout passage to receive nasal cleansing fluid from the opening of the container, the spout having a curved portion for directing nasal cleansing fluid toward a nasal passageway of a user when the container is clear of a nasal discharge path, the spout passage being continually open and unobstructed;

wherein the container is partially collapsible to force nasal cleansing fluid through the spout passage and into the nasal passageway.

BRIEF DESCRIPTION OF THE DRAWINGS

The following figures set forth embodiments of the invention in which like reference numerals denote like parts. Embodiments of the invention are illustrated by way of example and not by way of limitation in the accompanying figures.

DETAILED DESCRIPTION OF EMBODIMENTS OF THE INVENTION

Figure 1:
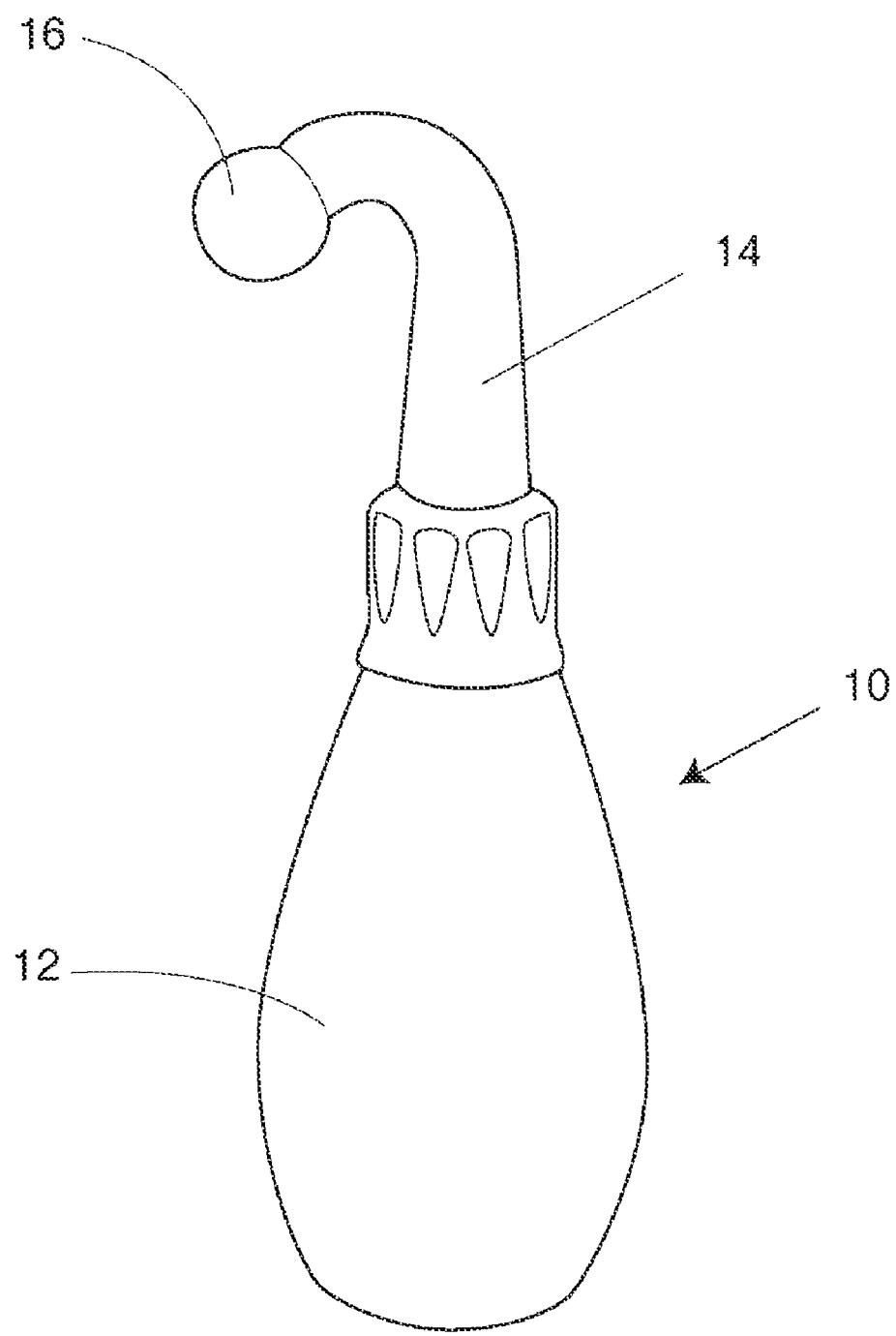
FIG. 1 is a perspective view of a nasal irrigation device according to an embodiment of the present invention.

Referring to FIG. 1, a nasal irrigation device according to an embodiment of the present invention is indicated by reference numeral 10. The nasal irrigation device 10 generally includes a container 12 and a spout 14 having a nose-engaging end 16.

Figure 2:
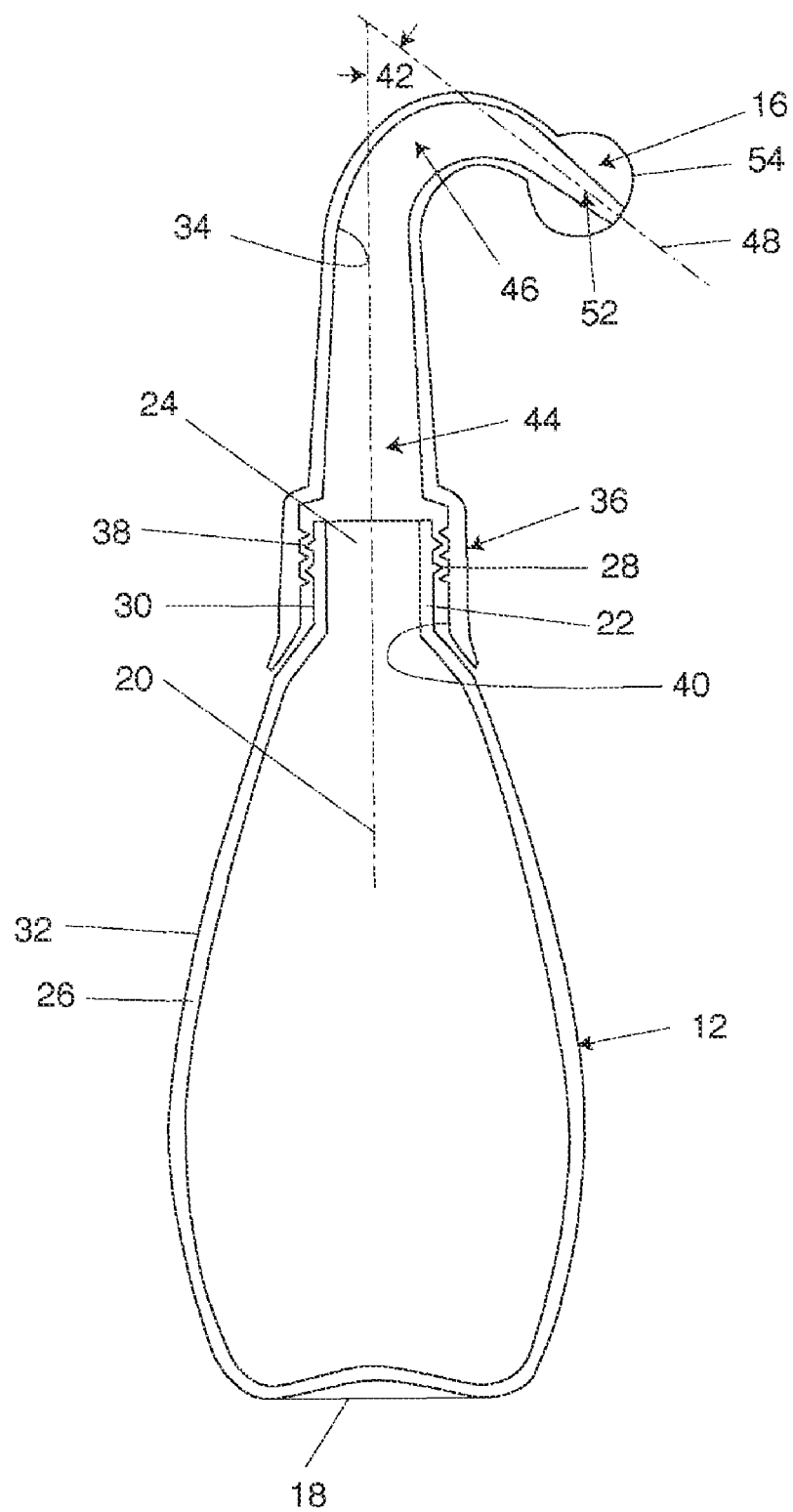
FIG. 2 is a side sectional view of the nasal irrigation device of FIG. 1.

Referring also to FIG. 2, the container 12 includes an opening 24, which is provided opposite a closed end 18 thereof. An axially extending flange 22 extends from a container body 26 and surrounds the opening 24. Threads 28 are provided on an outer surface 30 of the axially extending flange 22.

The container 12 is made of a plastic and the container body 26 is collapsible when pressure is applied to an outer surface 32 of the container body 26. The pressure applied should be sufficient to temporarily deform the container shape in order to force the container contents, which is typically a saline solution, out of the opening 24. Depending on the strength of the user and the rigidity of the container material, the user may use one or two hands to squeeze the container 12.

The container 12 is not limited to being made of plastic. Any suitable material that forms a collapsible container may be used.

The spout 14 is coupled to the container 12 so that a passage 34 of the spout 14 is aligned with the opening 24. The spout 14 includes a connecting end 36 that is coupled to the container 12 and the nose-engaging end 16, which is generally ball-shaped in order to provide a comfortable contact surface 54 for engagement with a user's nose. The connecting end 36 includes threads 38, which are provided on an inner surface 40 thereof. The threads 40 mate with threads 26 of the axially extending flange 22 to provide a threaded connection between the container 12 and the spout 14.

It will be appreciated by a person skilled in the art that although the container-spout connection is described as being a threaded connection, any suitable type of connection may be used. For example, the connecting end 36 of the spout 14 may be provided with an elastic portion that flexes during assembly and provides a seal once assembled.

The spout passage 34 follows the tapering contour of the spout 14 and includes a generally linear portion 44, a curved portion 46 and an outlet portion 52. The diameter of the spout passage 34 gradually reduces in diameter through each portion 44, 46 and 52 between the connecting end 36 and the nose engaging end 16 in order to accelerate the saline solution through the spout 14. An inner profile of the spout passage 34 is smooth and continuous in order to allow for efficient redirection of fluid flow through the spout passage 34.

Figure 3:
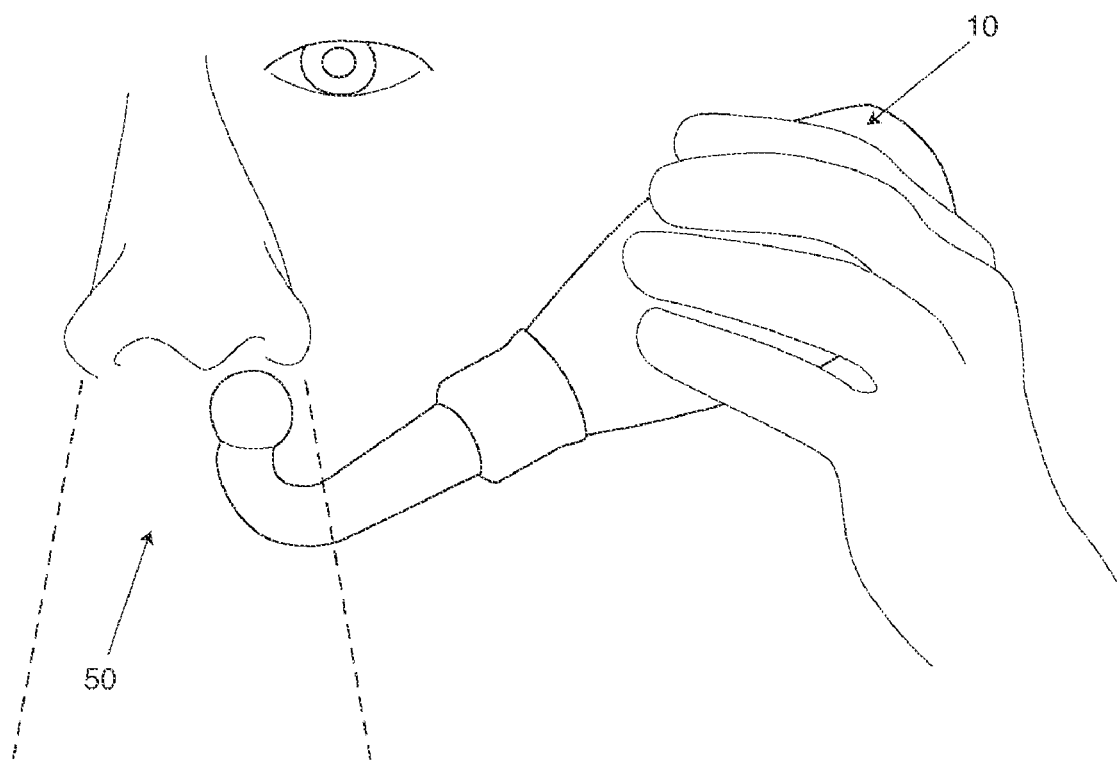
FIG. 3 is a view showing the nasal irrigation device of FIG. 1 in use.

The generally linear portion 44 initiates at connecting end 36 and is aligned with an axis 20 of opening 24. The outlet portion 52 of the spout passage 34 extends through the nose engaging end 16 and is aligned with an outlet axis 48. The curved portion 46 is located between the generally linear portion 44 and the outlet portion 52. An angle 42, which generally defines the amount of curvature of the curved portion 46, is provided between the axis 20 of the opening 24 and the outlet axis 48. In the embodiment of FIG. 1, the angle 42 is approximately 60 degrees; however, any angle in the range of 0 to 120 degrees may also be used. It will be appreciated by a person skilled in the art that an angle 42 of 0 degrees indicates that the curved portion 46 hooks around so that axes 20 and 48 are parallel but displaced from one another. The curved portion 46 is shaped to ensure that, in use, the container 12 is clear from a nasal discharge path 50 of the user, which is shown in FIG. 3.

The generally linear portion 44, the curved portion 46 and the outlet portion 52 of the spout passage 34 are not limited to having particular inlet and outlet diameters, however, diameters in the range of 15 to 40 mm for the generally linear portion 44, 10 to 20 mm for the curved portion 46 and 4 to 15 mm for the outlet portion 52 are preferred. In general, the spout 14 is sized so that the curved portion 46 is accessible by a cleaning implement, such as fingers or a small brush.

The tapering configuration of the spout passage 34 coupled with the smooth, continuous inner profile thereof facilitates easy and thorough cleaning and drying of the nasal irrigation device 10 following use. Thorough cleaning and drying of the device 10 avoids bacteria growth so that users are able deliver clean solution into their nasal passageways each time the nasal irrigation device 10 is used.

The spout 14 is made of plastic, however, it is not necessary that the spout 14 be collapsible similar to the container 12. The spout 14 is not limited to being made of plastic and instead may be made of any other suitable material. Examples of suitable materials include: fiberglass, glass, ceramic, and metals such as aluminum, stainless steel, copper. In addition, the spout 14 may include a metallic coating.

Use of the nasal irrigation device 10 will now be described with reference to FIG. 3. In preparation for use, container 12 is filled with a nasal cleansing fluid, such as saline solution, by removing the spout 14 and pouring the solution into the opening 24. Once the container 12 has been filled, the spout 14 is replaced on the container 12. The device 10 is then oriented as shown in FIG. 3 with the container 12 above the nose engaging end 16 of the spout 14 and the contact surface 54 of the nose engaging end 16 in contact with the user's nose. In this position, the outlet portion 52 of the spout passage 34 is directed into the user's nasal passage. No saline solution leaks out of the device 10 in this position because of the relatively large negative air pressure inside the container 12.

The user then squeezes the container 12 of the nasal irrigation device 10 with enough pressure to cause a partial collapse thereof. The partial collapse of the container 12 displaces a portion of the saline solution from the container 12 and forces the solution through the spout passage 34 and into the user's nasal passage. Saline solution that has been circulated by the nasal irrigation device 10 then exits the nose through the nasal passages. Because of the shape and orientation of the nasal irrigation device 10, the user's hands are clear of the nasal discharge path 50 and remain clean and dry during use.

Following use, the nasal irrigation device 10 is disassembled and hand washed or placed in a dishwasher for cleaning. The tapering of the spout 14 allows for better ventilation so that the nasal irrigation device 10 is able to dry efficiently and thoroughly before being re-used.

Figure 4:
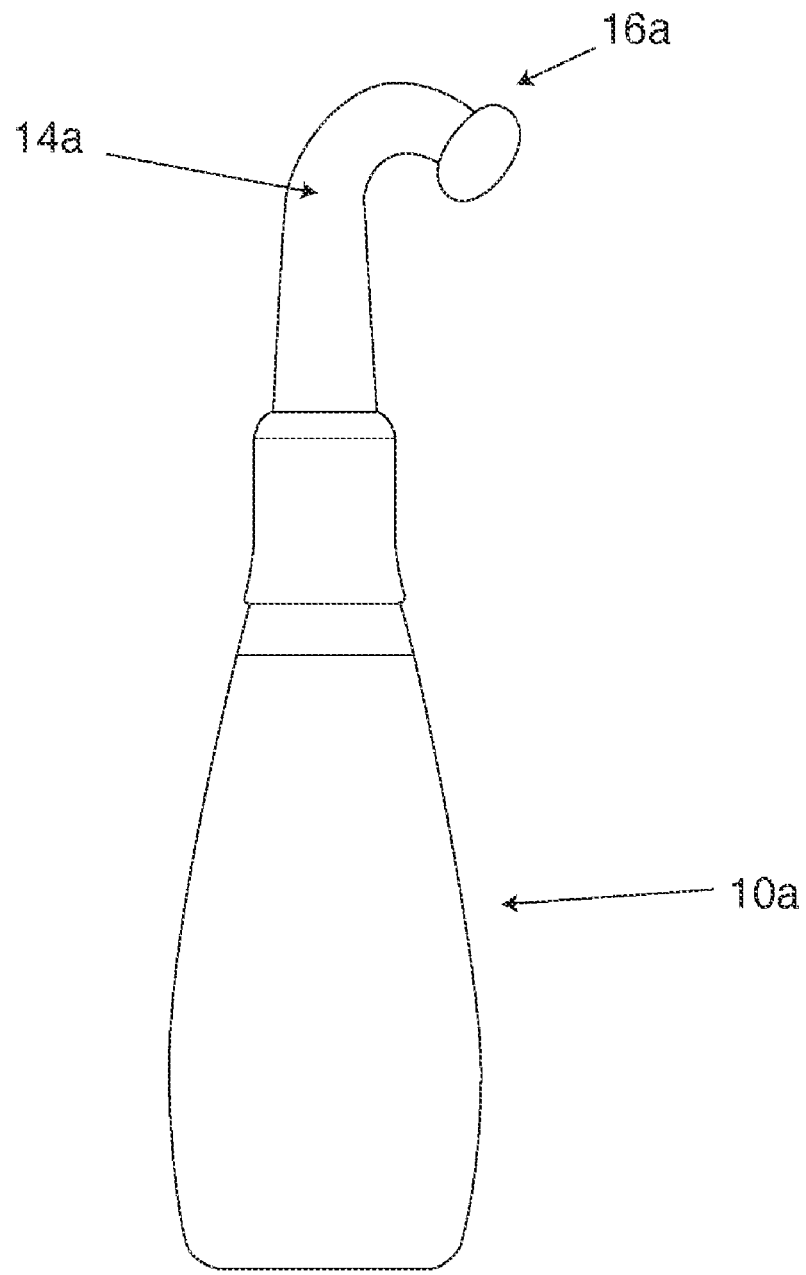
FIG. 4 is a side view of a nasal irrigation device according to another embodiment of the present invention.

Referring to FIG. 4 another embodiment of a nasal irrigation device 10 is generally indicated by reference numeral 10a. In this embodiment, a nose engaging end 16a of the spout 14a is a separate part and is coupled to the spout 14 by a threaded connection (not shown). In addition, an outlet portion (not shown) of a spout passage (not shown) is shorter than the outlet portion 52 of the nasal irrigation device 10 of FIG. 1, which results in the nose engaging end 16a appearing slightly flattened.

Figure 5:
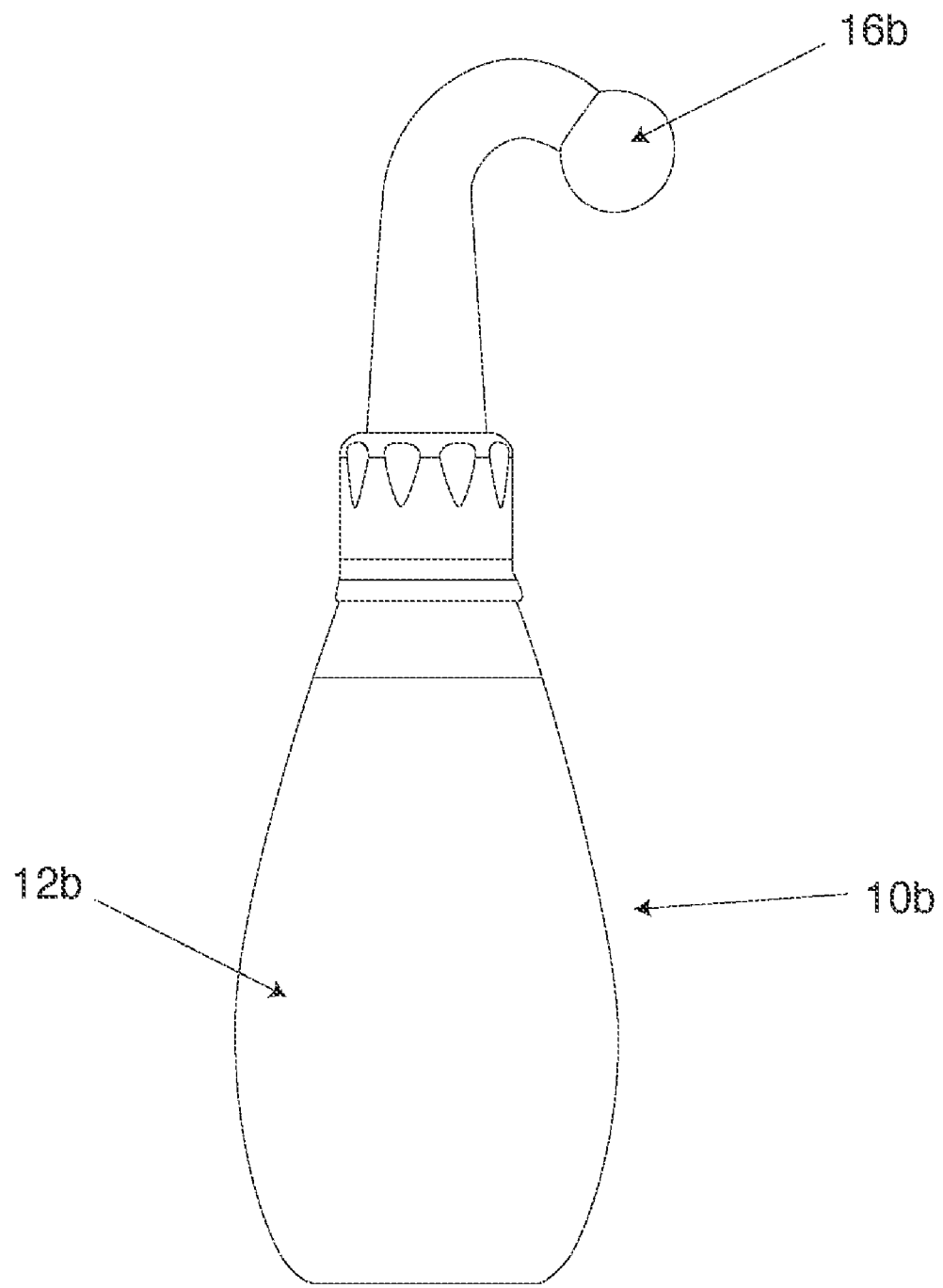
FIG. 5 is a side view of a nasal irrigation device according to yet another embodiment of the present invention.

Referring to FIG. 5, another embodiment of a nasal irrigation device 10 is generally indicated by reference numeral 10b. In this embodiment, nose engaging end 16b is a separate part similar to device 10b. In addition, container 12b is slightly shorter and has a larger internal diameter than the container 12 of the nasal irrigation device 10, of FIG. 1.

Figure 6:
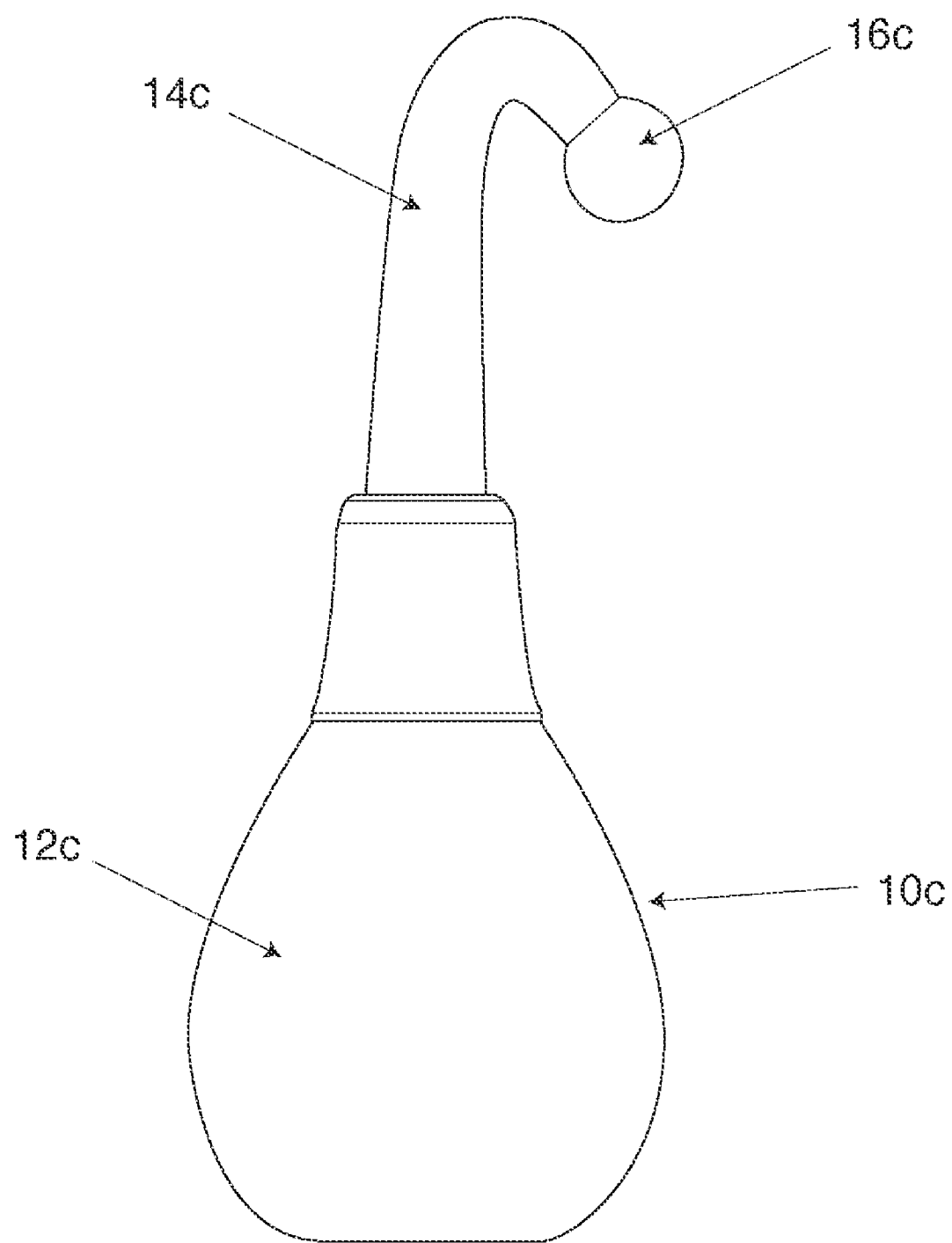
FIG. 6 is a side view of a nasal irrigation device according to still another embodiment of the present invention

Referring to FIG. 6 still another embodiment of a nasal irrigation device 10 is generally indicated by reference numeral 10c. In this embodiment, nose engaging end 16c is a separate part similar to devices 10b and 10c. In addition, spout 14c is elongated and container 12c is shorter and includes a larger internal diameter than the container 12 of FIG. 1. An angle (not shown) defining curved portion 44c is less than the angle 42 of the nasal irrigation device 10 of FIG. 1.

Figure 7:
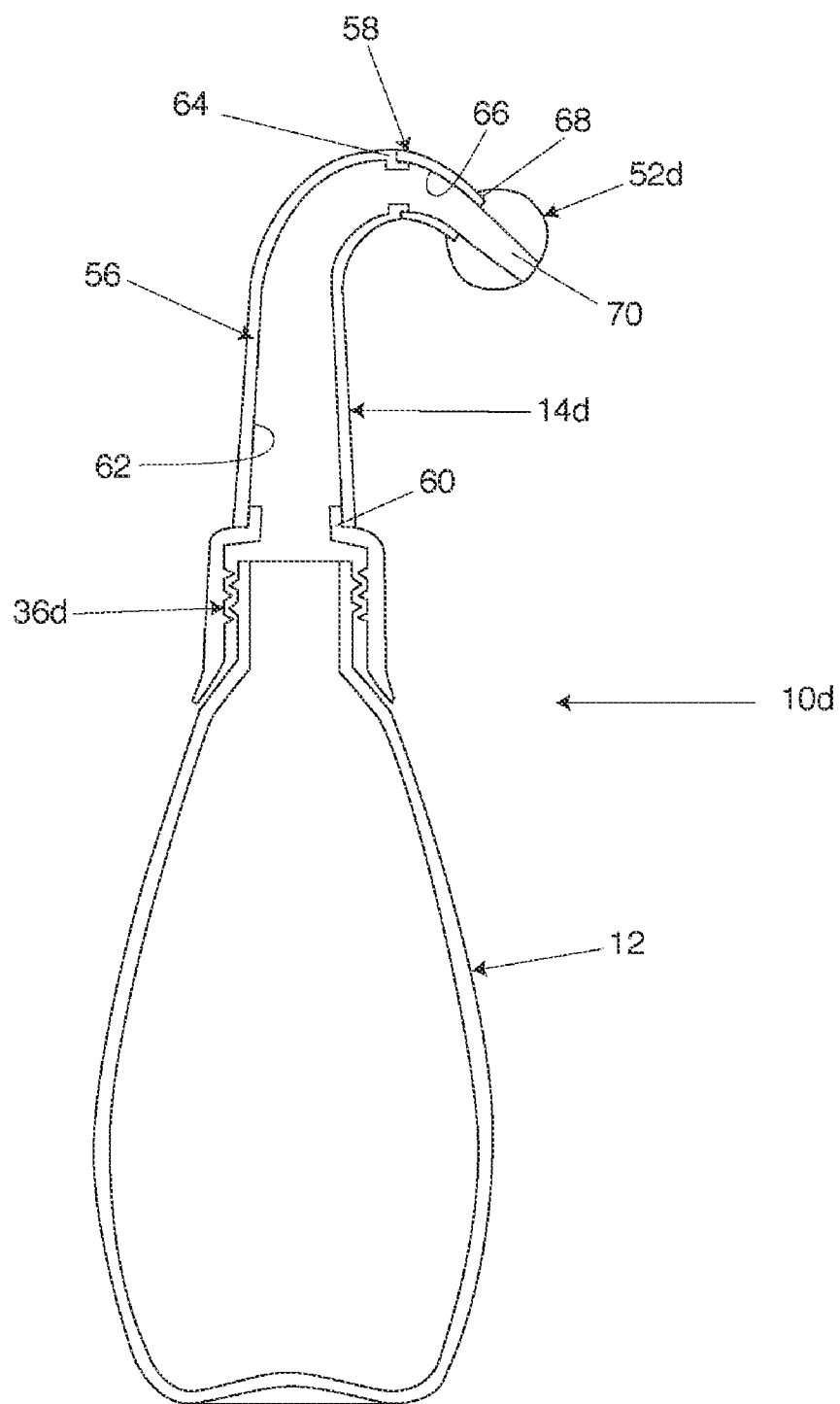
FIG. 7 is a side sectional view of a nasal irrigation device according to still another embodiment of the present invention.
Figure 8:
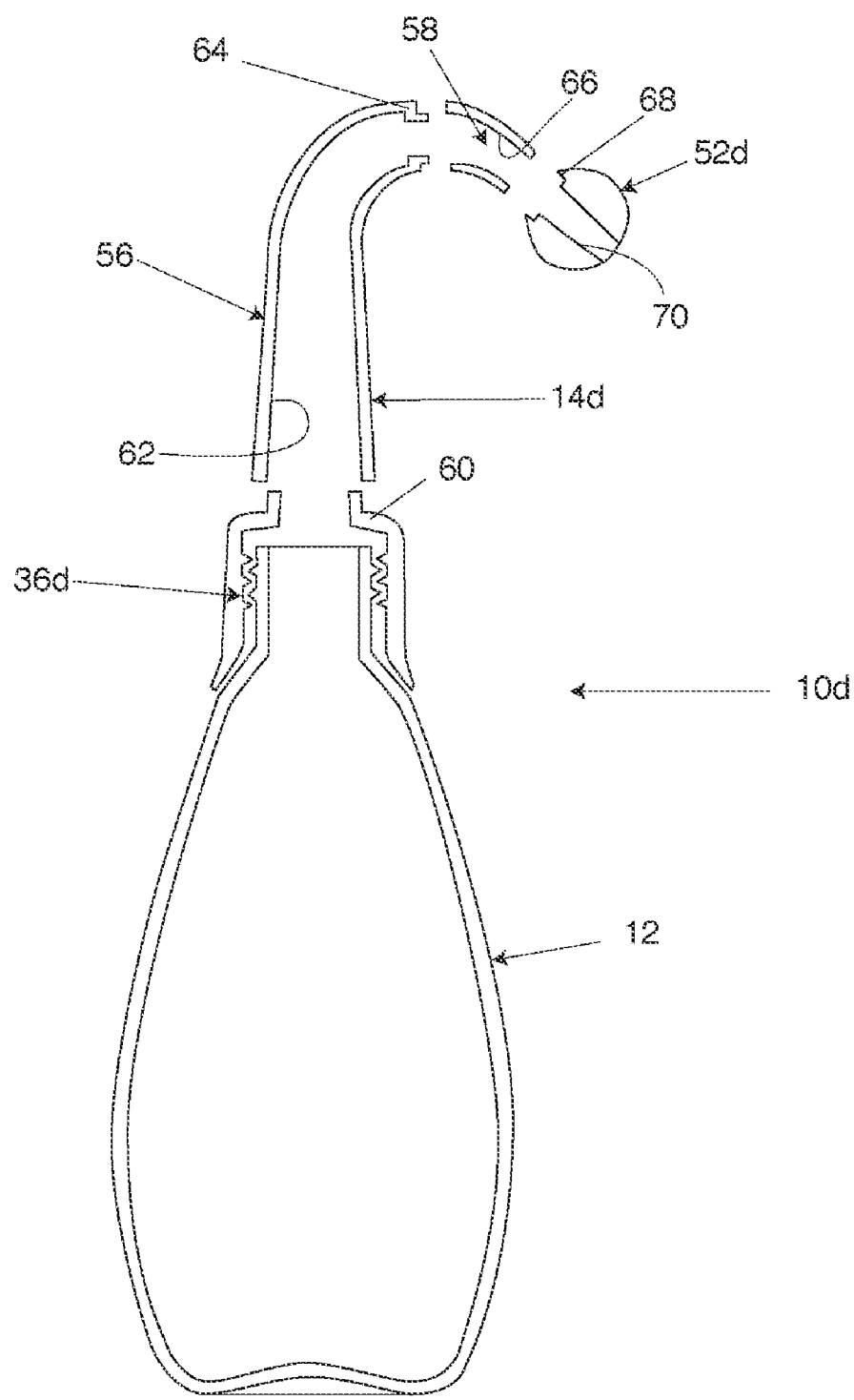
FIG. 8 is an exploded side sectional view of the nasal irrigation device of FIG. 7.

Another embodiment of a nasal irrigation device 10d is shown in FIGS. 7 and 8. In this embodiment, a spout 14d is made up of four different parts. A connector 36d, a first portion 56, a second portion 58 and an outlet portion 52d are coupled to one another to form the spout 14d. The connector 36d includes a flange 60 that abuts an inner surface 62 of the first portion 56. Similarly, first portion 56 includes a flange 64 that abuts an inner surface 66 of the second portion 58. A step 68 is provided in inner surface 70 of the outlet portion 52d for receiving the second portion 58.

Depending on the type of material selected for the parts of the spout 14d, the parts may be coupled to one another by glue, welding or another suitable fastener. Alternatively, the parts may be releasably coupled to one another by mechanical means, such as threads, for example. It will be appreciated by a person skilled in the art that an inner profile of each of the joints between spout parts is minimized so that the spout passage 34d, which extends through the entire spout 14d, is as smooth as possible.

In still another embodiment, the container 12 is replaced by a mechanical pumping device in order to provide a continuous flow of nasal irrigation fluid to the spout 14.

It will be appreciated that the nose engaging end 16 of the nasal irrigation device 10 is not limited to being ball-shaped. The end 16 may alternatively be flattened, as shown in FIG. 4, or even further flattened. Any shape may be provided as long as a contact surface 54 of the end 16 provides a comfortable contact surface for engagement with the user's nose. Similarly, the container 12 is not limited to the pear shape disclosed. The container 12 may be any suitable shape.

The nasal irrigation device 10 may be used with any type of nasal cleansing fluid known in the art. One such cleansing fluid is comprised of: sodium chloride, sodium bicarbonate, boric acid, aloe vera, methylparaben and propylparaben. The solid components are diluted into a volume of water and poured into the container 12 of the nasal irrigation device 10 in preparation for use. The water should be clean but does not necessarily need to be sterile. The solid components, when diluted, generally sterilize water from most water sources.

The solid components may be provided in pre-measured packet form so that a user may simply pour the packet into the container 12 of the device 10 and add a predetermined volume of water. The volume of water required for the weight of the packet contents would be provided on instructions on the packaging of the packet and/or the device 10.

Specific embodiments have been shown and described herein. However, modifications and variations may occur to those skilled in the art. All such modifications and variations are believed to be within the scope and sphere of the present invention.

The invention claimed is:

1. A nasal irrigation device comprising:
   a container having an opening, said container for storing nasal cleansing fluid;
   a spout having a connecting end, a generally linear portion, a curved portion and a nose engaging end, said nose engaging end comprising an outlet portion, said connecting end of said spout being removably coupled to said container to allow a spout passage to receive nasal cleansing fluid from said opening of said container, said curved portion providing an angle between said generally linear portion and said outlet portion for directing nasal cleansing fluid toward a nasal passageway of a user when said container is clear of a nasal discharge path, said generally linear portion and said curved portion being tapered between said connecting end and said nose engaging end and said spout passage being continually open and unobstructed;
   wherein said container is partially collapsible to force nasal cleansing fluid through said spout passage;
   wherein an inner profile of said spout passage is smooth and continuous;
   said angle between said generally linear portion and said outlet portion of said spout provided by said curved portion is 60 degrees;
   a diameter of a generally linear portion of said spout is in the range of 15-40 mm;
   a diameter of said curved portion of said spout is in the range of 10-20 mm;
   a diameter of said outlet portion of said spout is in the range of 4-15 mm;
   said nose-engaging end is ball-shaped, said nose-engaging end providing a comfortable contact surface for engagement with a user's nose.

2. A nasal irrigation device as claimed in claim 1, wherein a tapering diameter of said spout passage is sized to allow said nasal irrigation device to dry thoroughly following use.

3. A nasal irrigation device as claimed in claim 1, wherein prior to use, said container is filled with said nasal cleansing fluid through said opening.

* * * * *